United States Patent
Wines

(10) Patent No.: US 11,918,508 B1
(45) Date of Patent: Mar. 5, 2024

(54) OSTOMY APPLIANCE FOR PROVIDING CUSTOMIZED AND LOCALIZED CONVEX SUPPORT

(71) Applicant: Hollister Incorporated, Libertyville, IL (US)

(72) Inventor: James P. Wines, Algonquin, IL (US)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 18/263,616

(22) PCT Filed: Apr. 25, 2023

(86) PCT No.: PCT/US2023/066160
§ 371 (c)(1),
(2) Date: Jul. 31, 2023

Related U.S. Application Data

(60) Provisional application No. 63/403,098, filed on Sep. 1, 2022.

(51) Int. Cl.
*A61F 5/445* (2006.01)
*A61F 5/44* (2006.01)
(Continued)

(52) U.S. Cl.
CPC .............. *A61F 5/445* (2013.01); *A61F 5/443* (2013.01); *A61F 5/448* (2013.01); *A61F 2005/4483* (2013.01)

(58) Field of Classification Search
CPC .......... A61F 5/445; A61F 5/443; A61F 5/448; A61F 2005/4483
See application file for complete search history.

(56) References Cited

U.S. PATENT DOCUMENTS 3,970,085 A * 7/1976 Mersan .................. A61F 5/445
604/339
4,219,023 A * 8/1980 Galindo .................. A61F 5/445
604/344
(Continued)

FOREIGN PATENT DOCUMENTS

EP    0381393 B1    6/1993
EP    1348412 B1    7/2011
(Continued)

OTHER PUBLICATIONS

International Search Report issued by ISA/EPO in connection with PCT/US2023/066160 dated Jul. 14, 2023.
(Continued)

*Primary Examiner* — Guy K Townsend
(74) *Attorney, Agent, or Firm* — Levenfeld Pearlstein, LLC

(57) ABSTRACT

An ostomy appliance that comprises a ring member and a rib member. The ring member has an interior surface and an engagement portion encircling a centrally-located input opening. The engagement portion comprises a plurality of spaced-apart flexible tabs extending radially inward into the input opening. The flexible tabs have an opening centrally located between opposing side edges. A plurality of spaced-apart teeth extend radially inward from the ring member. The teeth are in alignment with spaces between the plurality of flexible tabs. The rib member has a curved body portion, a dowel, pins and a notched section in the body portion. The rib member is removably securable to the ring member whereby the pins are insertable into openings of adjacent flexible tabs and one of the plurality of spaced-apart teeth is received within the notched section such that the notched section is seated on the inside surface of the tooth.

20 Claims, 7 Drawing Sheets

(51) Int. Cl.
*A61F 5/443* (2006.01)
*A61F 5/448* (2006.01)

(56) References Cited

U.S. PATENT DOCUMENTS

| | | | | |
|---|---|---|---|---|
| 4,419,100 A * | 12/1983 | Alexander | .............. | A61F 5/448 604/339 |
| 4,592,750 A * | 6/1986 | Kay | ...................... | A61F 5/4407 604/277 |
| 4,596,566 A * | 6/1986 | Kay | ...................... | A61F 5/4404 604/176 |
| 4,610,676 A * | 9/1986 | Schneider | ............... | A61F 5/448 604/339 |
| 4,834,731 A * | 5/1989 | Nowak | .................... | A61F 5/448 604/339 |
| 4,950,223 A * | 8/1990 | Silvanov | ................ | A61F 5/441 600/32 |
| 4,973,323 A * | 11/1990 | Kaczmarek | ............. | A61F 5/448 604/277 |
| 5,004,464 A * | 4/1991 | Leise, Jr. | ................ | A61F 5/448 604/338 |
| 5,163,930 A * | 11/1992 | Blum | ...................... | A61F 5/448 604/338 |
| 5,195,996 A * | 3/1993 | Edwards | ................. | A61F 5/448 604/338 |
| 5,257,981 A * | 11/1993 | Takahashi | ............... | A61F 5/448 604/338 |
| 5,429,625 A * | 7/1995 | Holmberg | ............... | A61F 5/448 604/338 |
| 5,607,413 A * | 3/1997 | Holmberg | ............... | A61F 5/448 604/338 |
| 5,730,735 A * | 3/1998 | Holmberg | ............... | A61F 5/448 604/338 |
| 6,071,268 A * | 6/2000 | Wagner | .................. | A61F 5/445 604/338 |
| 6,210,384 B1 * | 4/2001 | Cline | ...................... | A61F 5/448 604/338 |
| 6,673,056 B2 | 1/2004 | Metz et al. | | |
| 6,689,111 B2 * | 2/2004 | Mulhauser | ............. | A61F 5/445 604/332 |
| 6,740,067 B2 * | 5/2004 | Leise, Jr. | ................ | A61F 5/448 604/336 |
| 6,840,924 B2 * | 1/2005 | Buglino | .................. | A61F 5/448 604/344 |
| 7,258,661 B2 | 8/2007 | Davies et al. | | |
| 7,347,844 B2 * | 3/2008 | Cline | ...................... | A61F 5/448 604/338 |
| 7,857,796 B2 * | 12/2010 | Cline | ...................... | A61F 5/445 604/277 |
| 8,845,606 B2 * | 9/2014 | Nguyen-Demary | .... | A61F 5/445 604/338 |
| 8,998,862 B2 * | 4/2015 | Hanuka | .................. | A61F 5/4405 604/318 |
| 8,998,867 B2 * | 4/2015 | Sabeti | ................... | A61F 5/4405 604/335 |
| 9,149,265 B2 | 10/2015 | Ehrenreich | | |
| 9,345,612 B2 * | 5/2016 | Hanuka | .................. | A61F 5/448 |
| 9,517,157 B2 | 12/2016 | Hanuka et al. | | |
| 9,770,359 B2 | 9/2017 | Edvardsen et al. | | |
| 9,943,436 B2 * | 4/2018 | Nguyen-Demary | .... | A61F 5/445 |
| 10,335,509 B2 * | 7/2019 | Kutsukake | .............. | A61L 15/44 |
| 10,512,562 B2 | 12/2019 | Kavanagh et al. | | |
| 10,524,953 B2 * | 1/2020 | Hanuka | .................. | A61F 5/4404 |
| 10,537,461 B2 * | 1/2020 | Hanuka | .................. | A61F 5/441 |
| 10,653,551 B2 * | 5/2020 | Apolinario | ............. | A61F 5/441 |
| 10,893,974 B2 | 1/2021 | Nyberg | | |
| 2003/0088219 A1 * | 5/2003 | Metz | ...................... | A61F 5/448 604/339 |
| 2004/0006320 A1 * | 1/2004 | Buglino | .................. | A61F 5/448 604/344 |
| 2004/0193122 A1 * | 9/2004 | Cline | ...................... | A61F 5/445 604/332 |
| 2005/0054997 A1 * | 3/2005 | Buglino | .................. | A61F 5/443 604/332 |
| 2006/0206069 A1 * | 9/2006 | Cline | ...................... | A61F 5/448 604/332 |
| 2008/0119804 A1 * | 5/2008 | Cline | ...................... | A61F 5/448 604/338 |
| 2012/0059341 A1 * | 3/2012 | Masters | .................. | A61F 5/448 604/339 |
| 2012/0136324 A1 * | 5/2012 | Hanuka | .................. | A61F 5/441 604/318 |
| 2013/0030397 A1 * | 1/2013 | Sabeti | ................... | A61F 5/4405 604/338 |
| 2014/0316360 A1 * | 10/2014 | Ekfeldt | ................... | A61F 5/445 604/338 |
| 2014/0324002 A1 * | 10/2014 | Luce | ....................... | A61F 5/441 604/338 |
| 2016/0074206 A1 * | 3/2016 | Nassopoulos | ........... | A61F 5/445 604/338 |
| 2016/0302959 A1 * | 10/2016 | Kavanagh | ............... | A61F 5/449 |
| 2018/0333290 A1 * | 11/2018 | Jones | ...................... | A61F 5/442 |
| 2019/0231580 A1 * | 8/2019 | Czaplewski | ............ | A61F 5/448 |
| 2019/0254864 A1 * | 8/2019 | Czaplewski | ............ | A61F 5/451 |
| 2019/0380860 A1 * | 12/2019 | Eggert | ................... | A61F 5/4405 |
| 2020/0100931 A1 * | 4/2020 | Schoess | .................. | A61F 5/443 |
| 2020/0253777 A1 * | 8/2020 | Jones | ...................... | A61F 5/443 |
| 2021/0307952 A1 * | 10/2021 | Nielsen | .................. | A61F 5/448 |
| 2021/0369492 A1 * | 12/2021 | O'Grady | ........... | A61M 39/0247 |
| 2022/0168131 A1 * | 6/2022 | Heckler | .................. | A61F 5/449 |

FOREIGN PATENT DOCUMENTS

| | | |
|---|---|---|
| EP | 2370030 B1 | 10/2011 |
| EP | 2482767 B1 | 12/2015 |
| EP | 2950761 B2 | 12/2015 |
| EP | 2497449 B1 | 1/2016 |
| EP | 1485048 B1 | 6/2016 |
| EP | 3238671 B1 | 11/2017 |
| EP | 3270835 B1 | 1/2018 |
| EP | 2950761 B2 | 9/2020 |
| WO | 99/30653 A1 | 6/1999 |
| WO | 2015/132779 A1 | 9/2015 |
| WO | 2020/200382 A1 | 10/2020 |
| WO | 2020/220025 A1 | 10/2020 |
| WO | WO-2020200382 A1 * | 10/2020 ........... A61F 5/4404 |

OTHER PUBLICATIONS

Written Opinion ssued by ISA/EPO in connection with PCT/US2023/066160 dated Jul. 14, 2023.

* cited by examiner

OSTOMY APPLIANCE FOR PROVIDING CUSTOMIZED AND LOCALIZED CONVEX SUPPORT

This is a National Stage Application of International Patent Application No. PCT/US2023/066160, filed Apr. 25, 2023, which claims the benefit of and priority to U.S. Provisional Application No. 63/403,098, filed Sep. 1, 2022, the entireties of which are incorporated fully herein by references.

BACKGROUND

The present disclosure relates to ostomy appliances, and more particularly to a convex ring member for use with ostomy appliances for providing localized and customized convex support around a stoma.

Ostomy pouches for the collection of body waste output from a stoma are well known and used by individuals who have had surgery such as a colostomy, ileostomy or urostomy. Ostomy pouches are generally attached to a user via an ostomy barrier, which is configured to seal against peristomal skin surfaces and protect the peristomal surfaces from exposure to stomal effluent. However, the topography of stomas and peristomal surfaces surrounding stomas can vary among patients and providing a single ostomy appliance which can effectively seal against such different peristomal surfaces and stomas can be particularly challenging. For example, a stoma may protrude more or less, or may even be flush or recessed.

A person with an ostomy having a stoma that is flush or recessed may find that applying external support or pressure from a barrier in the peristomal region aids in directing the discharge of effluent from the stoma directly into the ostomy pouch which can prevent undesirable leakage of body waste output between the barrier and the pouch. Accordingly, the effectiveness of an adhesive seal between the ostomy barrier and the peristomal skin surface (i.e., a seal formed by the adhesive layer) may be prolonged. Thus, convex inserts and convex ostomy barriers, such as ADAPT® convex barrier rings available through the assignee of the present application, have been developed to apply pressure around such peristomal regions.

However, the convexity of a conventional convex ostomy barrier or insert is fixed and may not work efficiently for all ostomates. Thus, convex ostomy barriers and convex inserts of various convexity depths have been made available in the market. Further, an ostomate may wish to incrementally adjust the convexity of an ostomy barrier to achieve an optimal convexity for his/her topography of stoma.

Accordingly, for at least the above-noted reasons, there is a critical need in the art for a customizable ostomy appliance that can accommodate a variety of stomal features and provide a desired degree of convex support to particular localized regions around the stoma inlet/opening. There is further a desire to provide a customizable ostomy appliance that can provide varying degrees of support around the stoma inlet/opening and that can enable a user to adjust or set the amount of flexibility or rigidity to different support regions. There is further a need in the art for an ostomy appliance that can provide the necessary flexibility upon application without compromising the structural rigidity as a support when in use.

BRIEF SUMMARY

Embodiments presented herein are directed to an ostomy appliance comprising a ring member and a rib member. The ring member can have an interior surface and an engagement portion encircling a centrally-located input opening. The engagement portion can comprise a plurality of spaced-apart flexible tabs extending radially inward into the input opening. The flexible tabs can have opposing side edges and opposing interior and exterior surfaces with an opening extending therebetween. The opening can be centrally located between the opposing side edges. A plurality of spaced-apart teeth can extend radially inward from the inside surface of the ring member into the input opening. The teeth can be in alignment in a first direction with spaces between the plurality of flexible tabs and can have an inside surface facing the interior surface of the plurality of flexible tabs.

According to embodiments presented herein, the rib member can have a curved body portion with opposing inside and outside surfaces joined together by opposing top and bottom edges and opposing side edges. The rib member can have a dowel, pins and a notched section in the body portion. The dowel can extend radially inward from the inside surface of the body portion. The pins can extend axially away from the top edge of the body portion. The notched section can form a recess along the inside surface and bottom edge of the body portion. The rib member can be removably securable to the ring member whereby the pins of the rib member can be insertable into openings of adjacent flexible tabs of the plurality of flexible tabs and a first tooth of the plurality of spaced-apart teeth in alignment in the first direction with a space between the adjacent flexible tabs is received within the notched section of the rib member. The notched section can be seated on the inside surface of the tooth.

According to embodiments presented herein the ring member can further comprise an outer flange and a middle portion. The middle portion can be between the outer flange and the engagement portion and can be curved to elevate the engagement portion from the outer flange in the first direction. The plurality of spaced apart flexible tabs can encircle the entirety of the engagement portion and the input opening. Each of the plurality of spaced-apart tabs can be substantially equivalent in size and can be spaced a same distance apart from adjacent ones of the plurality of flexible tabs. A first distance can separate the openings of the adjacent flexible tabs and the pins of the rib member can be reciprocally spaced apart from one another by said first distance. The first tooth can be spaced halfway between the openings of the adjacent flexible tabs in a second direction perpendicular to the first direction. The ring member can be provided as an insert between layers of an ostomy barrier. The ring member can be removably securable to an ostomy barrier securable to a user. The plurality of spaced-apart flexible tabs can be curved. Upon being applied to a user, the inside surface of the plurality of flexible tabs can be configured to engage an adjacent parastomal region of the user and pull the adjacent parastomal region towards a pouch-side of the ring member. Upon securing the rib member to the ring member, the adjacent flexible tabs can have reduced flexibility. A plurality of rib members substantially identical to the rib member can be further provided, each of the plurality of rib members can be removably securable and repositionable between adjacent tabs of the plurality of flexible tabs and a tooth of the plurality of spaced apart teeth positioned between the adjacent tabs.

Embodiments presented herein are further directed to a convex support for an ostomy appliance. The convex support can comprise an annular ring member having an interior surface and an engagement portion encircling a centrally-located input opening. The engagement portion can comprise a plurality of spaced-apart flexible tabs extending radially inward into the input opening. The flexible tabs can have opposing side edges and opposing interior and exterior surfaces with an opening extending therebetween. The opening can be centrally located between the opposing side edges. A plurality of spaced-apart teeth can extend radially inward from the inside surface of the ring member into the input opening. The teeth can be in alignment in a first direction with spaces between the plurality of flexible tabs and can have an inside surface facing the interior surface of the plurality of flexible tabs.

According to embodiments presented herein, the convex support can further comprise a rib member. The rib member can have a curved body portion with opposing inside and outside surfaces joined together by opposing top and bottom edges and opposing side edges. The rib member can have a dowel, pins and a notched section in the body portion. The dowel can extend radially inward from the inside surface of the body portion. The pins can extend axially away from the top edge of the body portion. The notched section can form a recess along the inside surface and bottom edge of the body portion. The rib member can be removably securable to the ring member whereby the pins of the rib member can be insertable into openings of adjacent flexible tabs of the plurality of flexible tabs and a first tooth of the plurality of spaced-apart teeth in alignment in the first direction with a space between the adjacent flexible tabs is received within the notched section of the rib member. The notched section can be seated on the inside surface of the tooth.

According to embodiments presented herein the plurality of flexible tabs of the convex support can comprise sixteen tabs that encircle the entirety of the engagement portion and the input opening. Each of the sixteen tabs can be substantially equivalent in size and being spaced a same distance apart from one another. The plurality of spaced-apart teeth can comprise sixteen teeth equivalently spaced apart from one another around the interior side of the ring member. A plurality of rib members substantially identical to the rib member can further be provided and the plurality of rib members can be of a quantity between two and eight. The plurality of spaced-apart teeth can comprise a distal end having an elevated barbed section to retain the rib member thereon. The plurality of spaced-apart teeth can comprise the first tooth, a second tooth and a third tooth located in sequence along a portion of the ring member and the plurality of spaced apart flexible tabs can comprise a first and second tab. The first tab can be aligned in the first direction between the first tooth and the second tooth and the second tab can be aligned in the first direction between the second tooth and the third tooth.

According to embodiments presented herein, the rib member of the convex support can be secured to the ring member. A first portion of the bottom edge of the body portion can be between the first tooth and the second tooth and a second potion of the bottom edge of the body portion can be between the second tooth and the third tooth. The rib member can comprise a first rib member and a second rib member substantially identical to the first rib member. The first and second rib members can be securable to the ring member in adjacent positions alongside one another and upon being secured in the adjacent positions, the first tooth can be between one of the opposing side edges of the first rib member and one of an opposing side edge of the second rib member. The rib member can be securable to the ring member by being snap fit thereon whereby the outside surface of the rib member snaps into place against the interior surface of the ring member.

Other objects, advantages and features of the present disclosure will be understood and appreciated by persons of ordinary skill in the art from consideration of the following specification taken in conjunction with the accompanying drawings.

DETAILED DESCRIPTION

Figure 1:
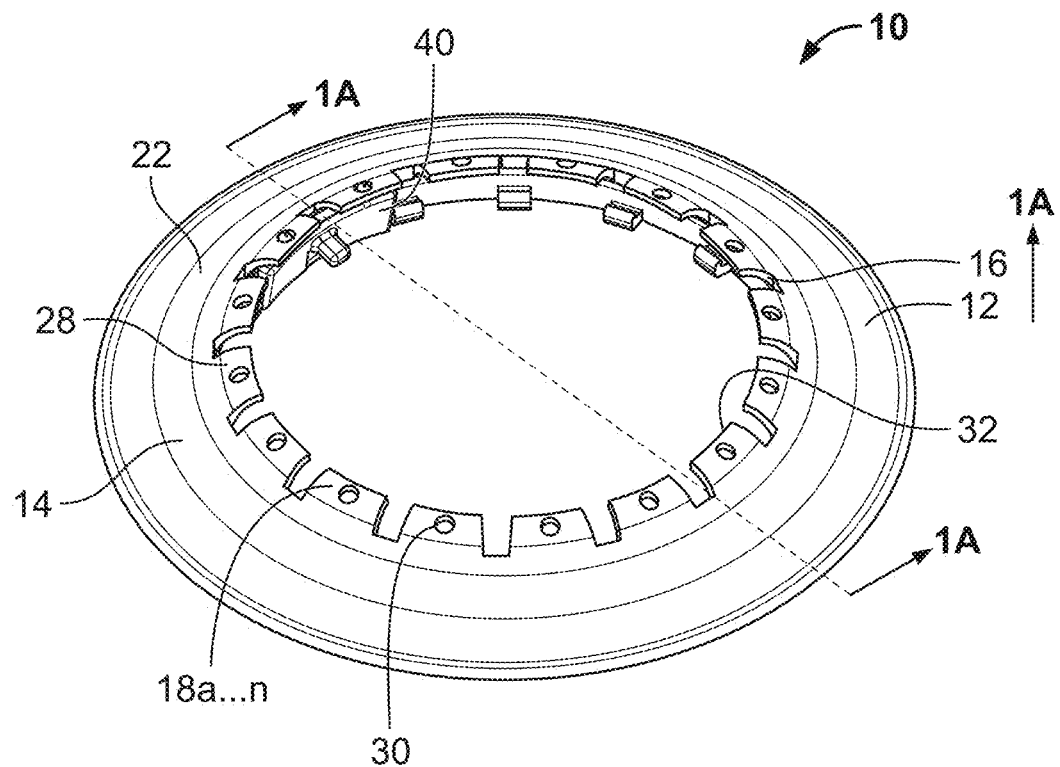
FIG. 1 is a body-side perspective view of a ring member according to embodiments presented herein.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

Figure 2:
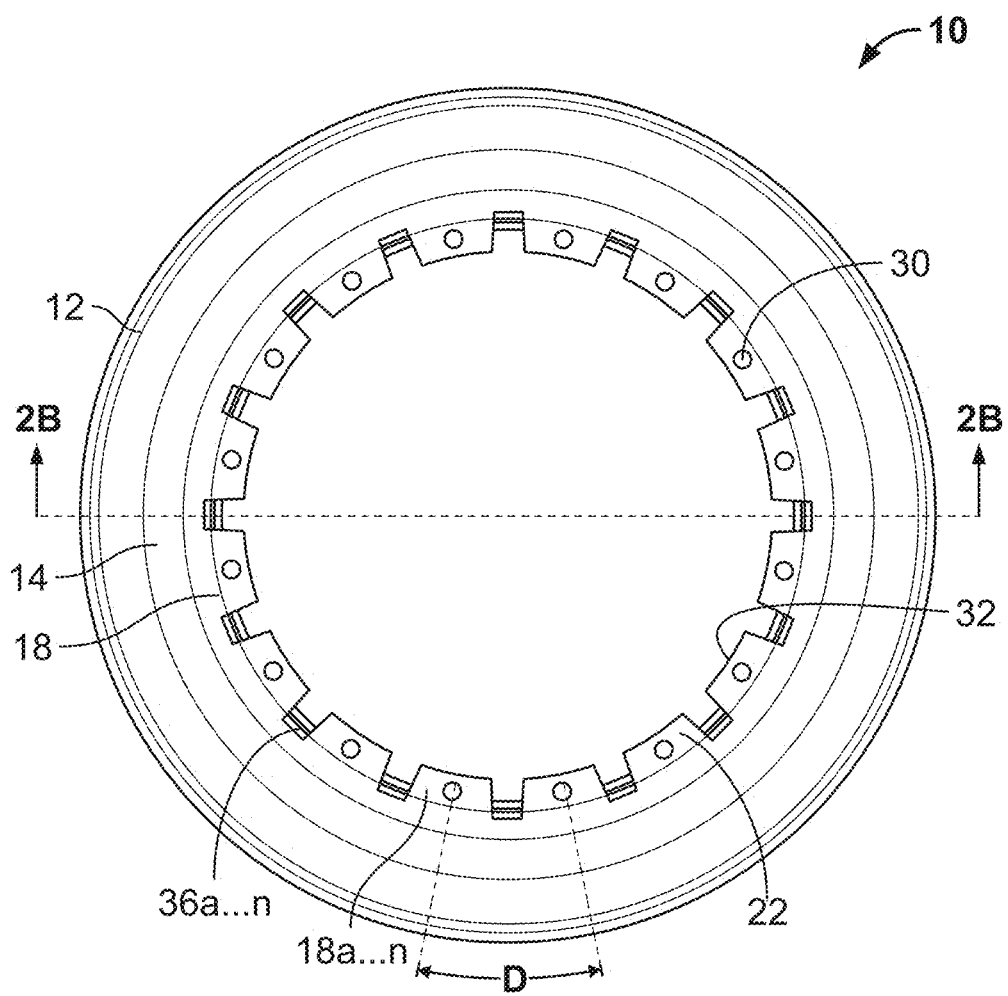
FIG. 2 is a body-side plan view of the ring member according to embodiments presented herein.
Figure 2A:
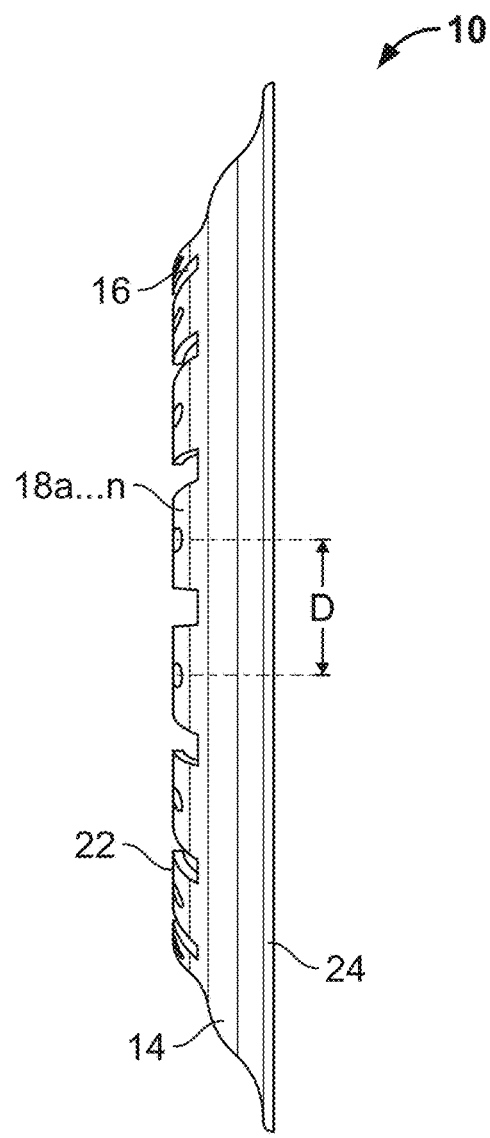
FIG. 2A is a side elevation view of the ring member of FIG. 2.

Referring now to the accompanying figures, and FIGS. 1-2 in particular, a convex ring member 10 is shown according to embodiments. As shown schematically in FIG. 1, convex ring member 10 can have an outer flange 12, a middle portion 14 and an interior stoma engagement portion 16 comprising a plurality of spaced apart flexible tabs 18a . . . n arranged around an inlet opening configured for receiving at least a portion of a stoma. According to embodiments, convex ring member 10 can be securable to, or integrated within, an ostomy skin barrier (not shown) and protrude axially toward a body-side direction to provide a convex ring-like shaped body configured to apply pressure around the peristomal area. More particularly, as shown in FIG. 2A, convex ring member 10 can have a body-side surface 22 and an ostomy pouch-side surface 24 that can be securable to the ostomy barrier which can in turn be removably coupled or secured to an ostomy pouch (not shown). Alternatively, convex ring member can be provided as an insert between layers of an ostomy barrier.

Figure 1A:
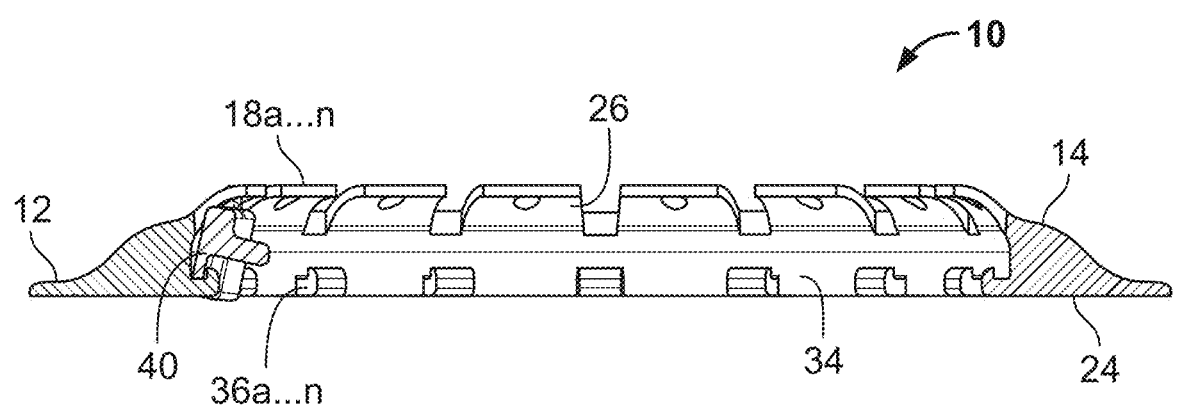
FIG. 1A is a cross sectional view of the ring member of FIG. 1 taken along the line 1A-1A of FIG. 1.

As shown schematically in FIGS. 1 and 1A, middle portion 14 between outer flange 12 and engagement portion 16 can have a curved or elevated contour to provide depth to ring member 10. According to embodiments convex ring member 10 including outer flange 12, middle portion 14 and engagement portion 16 can be comprised of a flexible biocompatible material such as silicone or other polymeric materials which can allow the ring member 10 to bend or flex. Such flexibility can be important upon application of the ring member 10 to the user as well as from the perspective of flexibly supporting the peristomal region. As shown in FIGS. 1 and 2, ring member 10 can have an annular configuration with a round outer edge. It will be understood however that ring member 10 can have alternate shapes and sizes without limitation.

As best shown in FIGS. 1-2, flexible tabs $18a \ldots n$ can be arranged entirely around engagement portion 16 and extend radially inward into the inlet opening. Tabs $18a \ldots n$ can have side edges and opposing interior and exterior surfaces 26, 28 with a thickness therebetween. As shown in FIGS. 1-2, an opening 30 can extend through the thickness of each of the tabs $18a \ldots n$. Opening 30 can be centrally located between the side edges of tabs $18a \ldots n$. As shown schematically in FIGS. 1-2, tabs $18a \ldots n$ can have a distal end 32 having a smooth surface suitable for engagement with locations of the peristomal surface. Tabs $18a \ldots n$ can taper as they extend inward toward distal end 32 such that the side edges are closer together at the distal end 32 than at an opposing proximal end adjacent middle potion 14. As shown in FIGS. 1A and 2A, tabs $18a \ldots n$ can have a bowed or curved shape between the proximal and distal 32 ends. In ordinary use, it will be understood that when ring member 10 is being applied to a user, it may be configured to press against the peristomal skin to facilitate the stoma to project outward to better direct discharge into an associated pouch.

According to embodiments shown schematically in FIGS. 1 and 2, tabs $18a \ldots n$ can be evenly spaced apart from one another with gaps or recesses therebetween; the recesses being defined by the side edges of adjacent tabs. As shown in FIGS. 1 and 2, tabs $18a \ldots n$ can be identically sized and evenly spaced around the entirety of engagement portion 16 such that the distance between centrally-located openings 30 of adjacent tabs can be consistent around the entirety of engagement portion 16. Similarly, the size of the recesses between adjacent tabs $18a \ldots n$ and distance between adjacent recesses can also be substantially identical around the entirety of engagement portion 16. For example, the size of the recesses between adjacent tabs $18a \ldots n$ and distance between adjacent recesses can be such that there is no functional difference between them around the entirety of engagement portion 16.

Figure 2B:
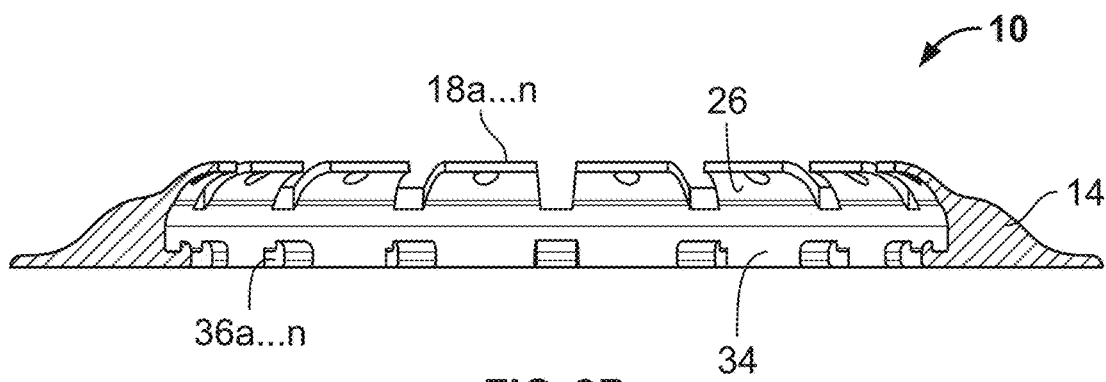
FIG. 2B is a cross sectional view of the ring member of FIG. 2 taken along the line 2B-2B of FIG. 2.

FIGS. 1A and 2B illustrates a cross-section views of ring member 10. As shown schematically in FIGS. 1A and. 2B, ring member 10 can have an interior surface 34 between the underside of the interior surface of the tabs $18a \ldots n$ and the body-side 22 of ring member According to embodiments shown in FIGS. 1A and 2B, a plurality of flange-like teeth $36a \ldots n$ can radially extend inward from the interior surface 34 of ring member 10 toward the inlet opening. As shown schematically in FIGS. 1A and 2B, the teeth $36a \ldots n$ can have a bottom surface that can be flush with the pouch-side 24 of the ring member 10 and an opposing top surface having a hook-like configuration comprising an proximal grooved portion adjacent the inside surface 34 of the insert and a distal barbed portion comprising an upwardly extending projection. As shown schematically in FIG. 1-2, interior surface 34 of ring member can be circular and at least partially define the inlet opening and be suitable for receiving a stoma therethrough.

Figure 3:
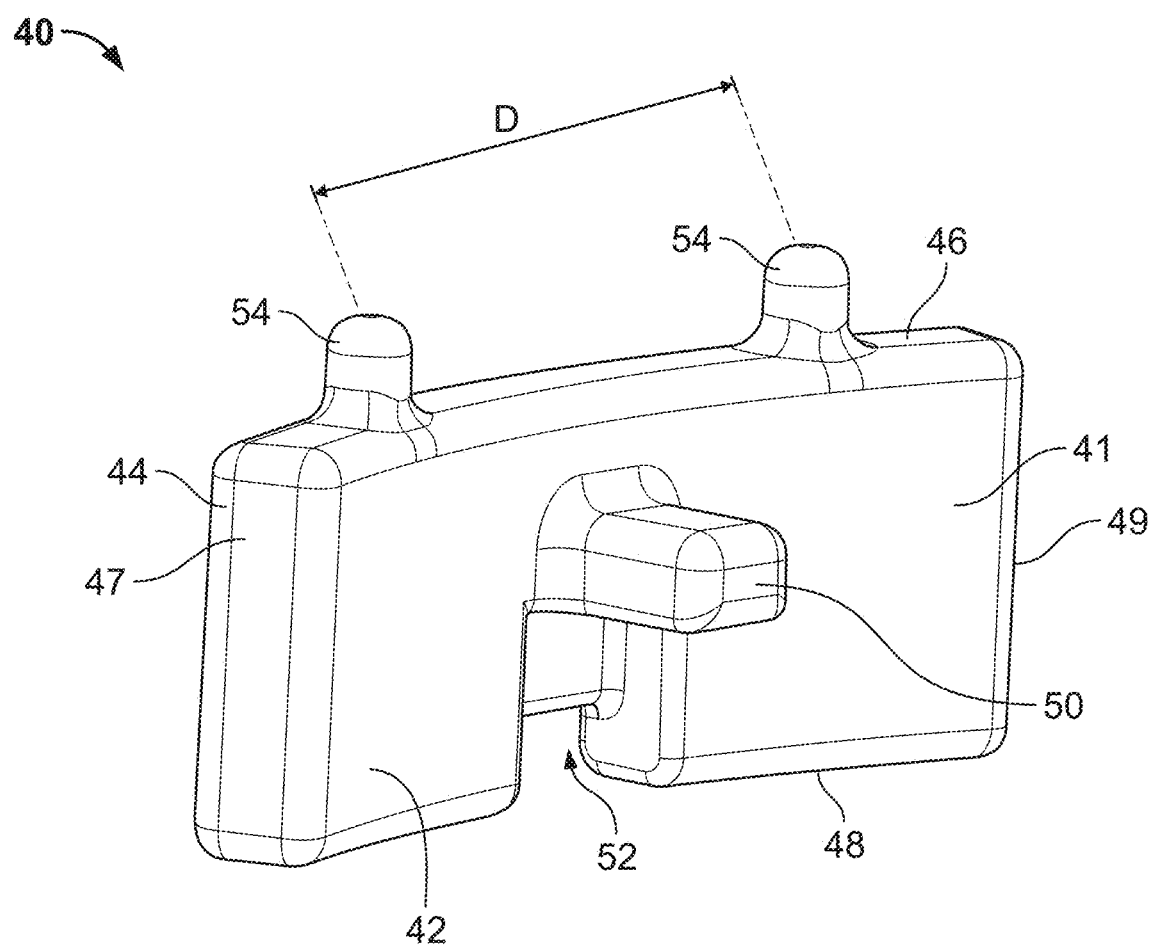
FIG. 3 is a perspective view rib member according to embodiments presented herein.

FIG. 3 illustrates an insertable rib member 40 according to embodiments. As shown schematically in FIG. 3, rib member 40 can have a body portion 41 with opposing inside and outside surfaces 42, 44 joined together by opposing top and bottom edges 46, 48 and opposing side edges. The body portion 41 of rib member 40 can have a curved or arcuate orientation whereby opposing the opposing side edges curve inward toward the inside surface 42. As described in further detail below, rib member 10 can engage along the inside surface 34 of ring member 10 via snap fit and the curvature of body portion 41 can correspond to that of the interior surface 34 of the ring member.

According to embodiments shown schematically in FIG. 3, rib member 10 can have a dowel 50 extending radially inward from the inside surface 42 of body portion 41 and a notched section 52 along the bottom edge 48. As shown schematically in FIG. 3, both dowel and notched section 52 can be centrally located along the body portion 41 between the opposing side edges with the notched section extending below an underside of the dowel 50 to the bottom edge 48 of rib member 40. It will be understood, however, that either or both of dowel 50 and notched section 52 can be positioned at other locations along rib member 40 and that rib member 40 can have a plurality of dowels and notched sections without limitation. As best shown in FIG. 3, notched section 52 can form recesses within both the bottom edge and within the interior side of the body portion 41 of rib member 40. At least a portion of notched section 52 can also have a back ledge extending downward below dowel 50.

As shown schematically in FIG. 3, rib member 40 can have spaced-apart pins 54 extending orthogonally from the top edge 46 of the body portion 41. Pins 54 can be spaced apart from one another by a distance D. Pins 54 can be adapted to be insertable within the openings 30 of tabs $18a \ldots n$ and it will be understood from the subject disclosure that distance D can correspond to the space between openings 30 in adjacent tabs 18 on ring member 10. According to embodiments shown schematically in FIG. 3, pins 54 can also be horizontally spaced from the center of the notched section 52 by a distance on the order of ½ D, and thus notched section 52 can be horizontally positioned half way between pins 54. As described in further detail below, such orientation can enable rib member 40 to be removably secured along the interior surface 34 of ring member 10.

FIGS. 1 and 1A illustrate ring member 10 with a rib member 40 secured thereto in one representative location of a plurality of locations. According to embodiments, one or more rib members 40 can be removably secured to ring member 10 as shown in FIGS. 1 and 1A by being snap fit thereon. As shown in FIGS. 1 and 1A, upon securing rib member to ring member 10, the pins 54 of rib member can be inserted into the openings 30 of adjacent flange members 18 from below and the body portion of rib member can be pressed against the interior surface 34 of ring member 10 such that the outside surface 44 of rib member is flush against or adjacent the inside surface 34 of ring member 10. Upon being pressed into ring member 10, notched section 52 of along the bottom edge 48 of rib member 40 can receive, engage and be seated upon a tooth 36 located between adjacent tabs 18. More particularly, the downwardly facing edge of the ledge of notched section 52 can be seated within the groove along the top surface of the tooth 36 and held in place by the upwardly projecting barb at the distal end of the tooth.

Thus, as can be seen in FIGS. 1 and 1A, rib member 40 and ring member can be correspondingly sized such that rib member 40 can be held securely in place below adjacent flexible tabs 18 and a tooth 36 located therebetween whereby the bottom of the rib member 40 is supported by the top surface of the tooth 36 and the top of the rib member is supported by the underside of adjacent tabs 18, and more particularly by engagement of the pins 54 within openings 30. According to embodiments shown schematically in FIG. 1, when the rib member is secured to the ring member 10, the sides of the body portion of rib member are flush against or adjacent side edges of alternating teeth 36a . . . n. As can be seen in FIGS. 1 and 1A, when secured together, the dowel 50 of rib member can extend radially inward toward the inlet opening. In such configuration, support can be facilitated by the rib member(s) 40 preventing the associated tabs 18 from folding towards the interior surface 34 of the ring member 10 thus providing a more rigid localized support at the stomal area adjacent the rib member(s) 40.

According to embodiments presented herein, the convex ring member 10 can be applied to a user by inserting the stoma through the inlet opening such that the ring member 10 encircles the stoma with the body side 22 facing inward towards the user's body and the pouch-side 24 is facing outward away from the user. In placing the ring member 10 around the stoma, the soft, flexible composition of the ring member 10 and tabs 18a . . . n can gently push on the peristomal skin surrounding the stoma to protrude or project the stoma outward to aid in directing the discharge of effluent from the stoma directly into the ostomy pouch. Upon being applied around the stoma, the user can apply the rib members 40 as desired.

From the subject disclosure, it will be recognized and appreciated, that upon application of ring member 10 around a stoma, the rib members 40 can be snapped into place along the ring member 10 at particular locations where the adjacent stomal area requires deeper convexity or additional firmness or rigidity to be adequately supported. According to embodiments, it will be recognized that the ring member 10 can alternatively be applied to a user with the rib members 40 already in place, such as for example, where a user has knowledge and familiarity with stomal locations that are in need of deeper convexity support and has previously customized the appliance accordingly.

It will be recognized that such capabilities can provide a more customizable ostomy appliance that is adjustable to suit the particular conditions or needs of an individual user. It will be further recognized that such capabilities can reduce the need for providing, or manufacturing multiple different types of specialized ostomy appliances to attempt to suit different individuals which can be commercially impractical. Accordingly, embodiments presented herein can provide adjustable convexity to account for stomal variations between individual users and also stomal changes that may evolve over time with regard to a specific individual user who may need additional support to different areas at different times. According to embodiments presented herein, such individual can add or reduce support to particular stomal areas by modifying use and positioning of the rib members 10. It will be appreciated that such functionality can better prevent undesirable leakage of body waste output which can improve sanitation and reduce embarrassment.

Figure 4A:
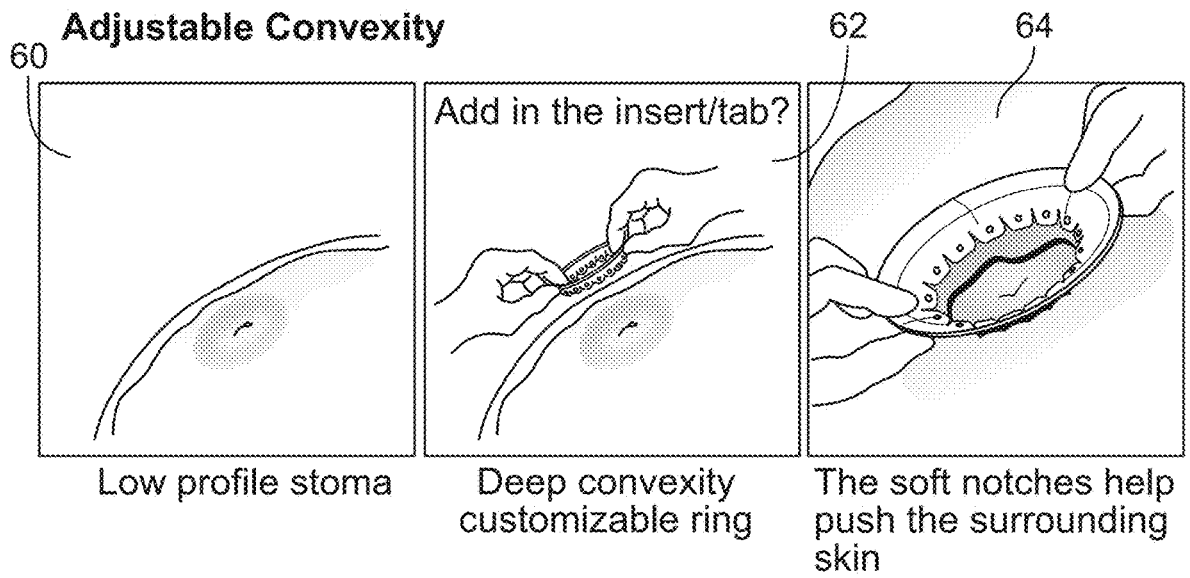
FIGS. 4A and 4B are perspective side-by-side views of a sequence of applying a ring member according to embodiments presented herein.
Figure 4B:
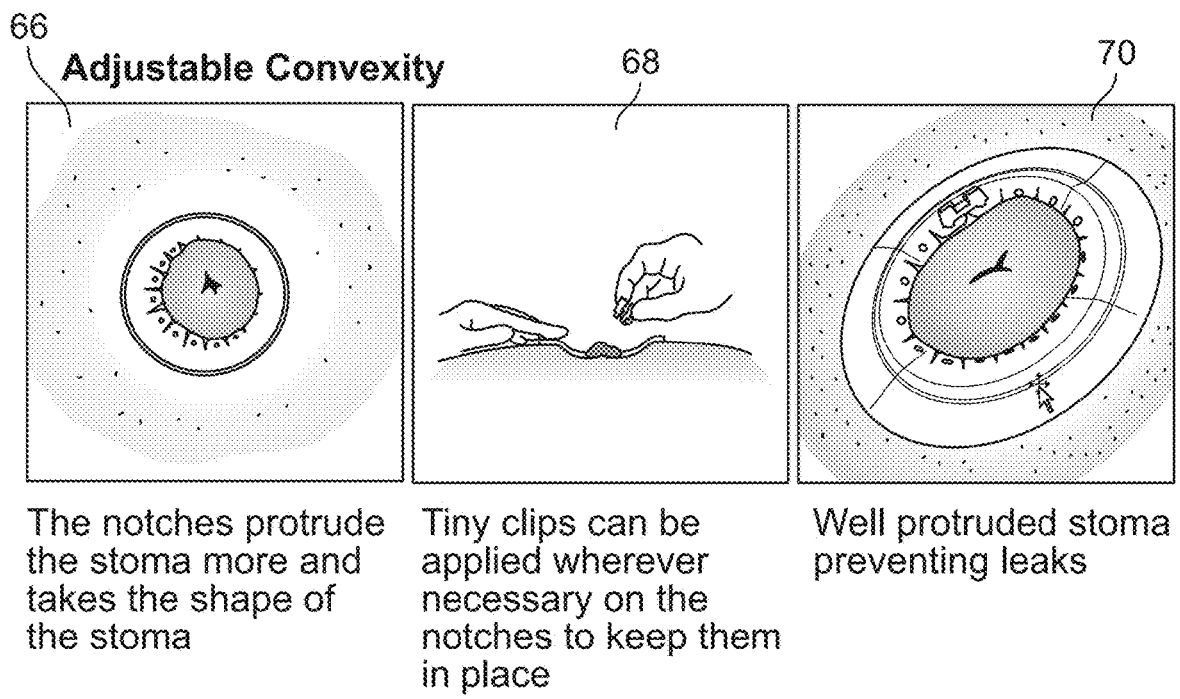

FIGS. 4A and 4B illustrate a sequence for applying and adjusting a convex adjustable ring member according to embodiments presented herein. As shown schematically in FIGS. 4A and 4B, a low profile stoma 60 is shown and a deep convex customizable ring member 10 of the type presented herein is applied 62 around the stomal area. During such application, the soft flexible tabs 18a . . . n help push 64 the surrounding skin of the peristomal area. Once applied, the flexible tabs 18a . . . n protrude the stoma 66 more and take the shape of the stoma. According to embodiments shown schematically in FIG. 4B, the rib member(s) 40 can be applied 68 to the ring member 10 to keep them in place and for added support. The result 70 can be a well-protruded stoma that can better prevent leakage.

Figure 5:
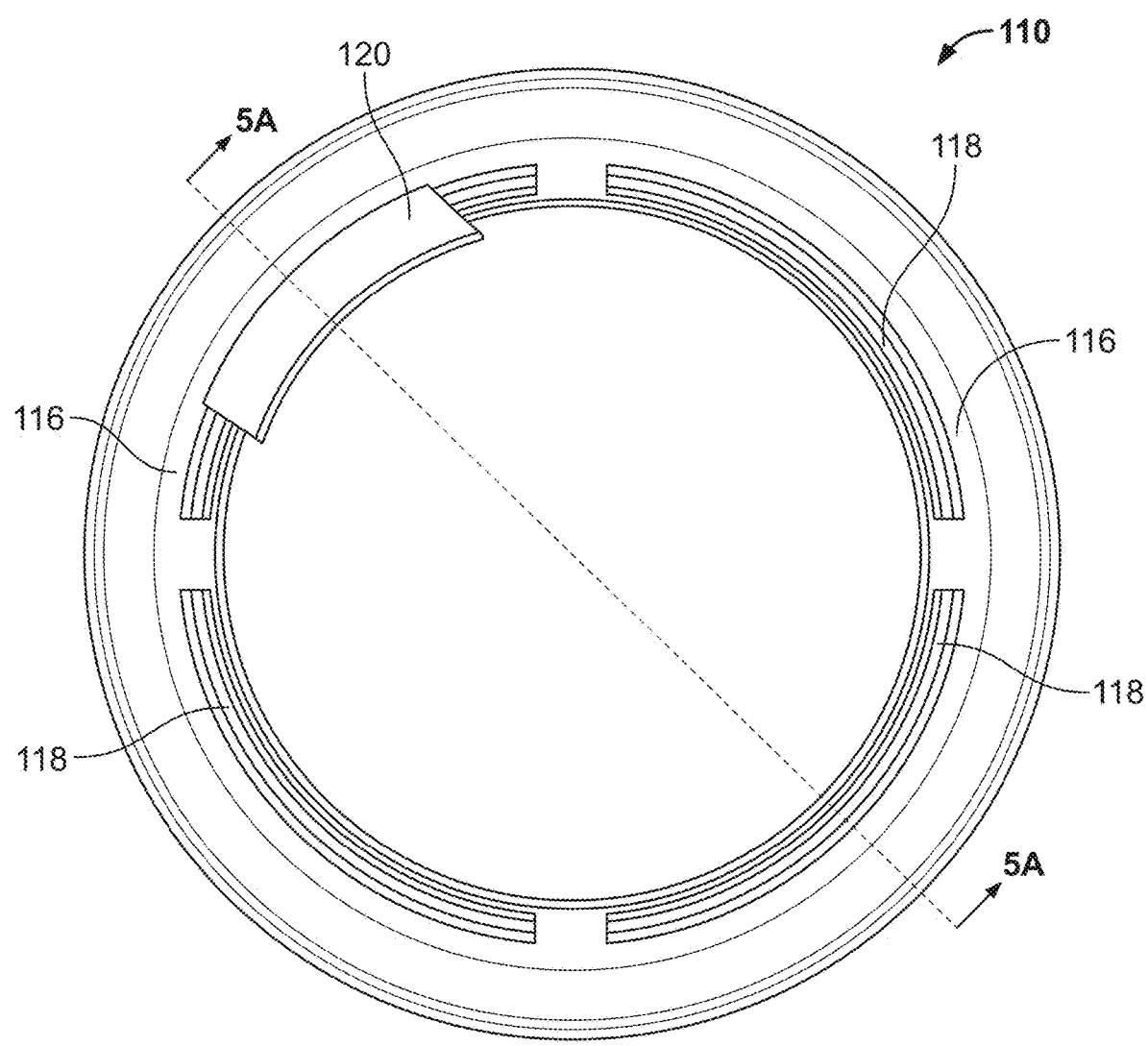
FIG. 5 is a body-side plan view of the ring member according to embodiments presented herein.
Figure 5A:
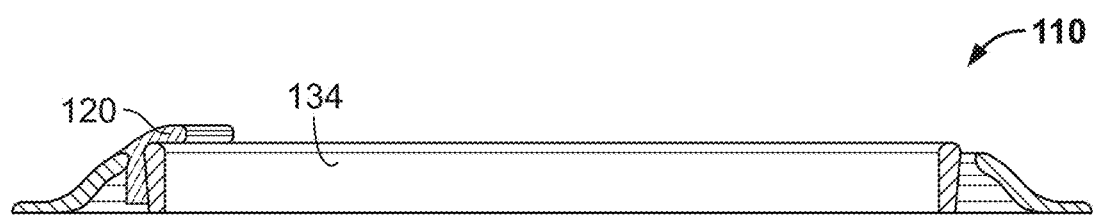
FIG. 5A is a cross sectional view of the ring member of FIG. 5 taken along the line 5A-5A of FIG. 5.
Figure 6:
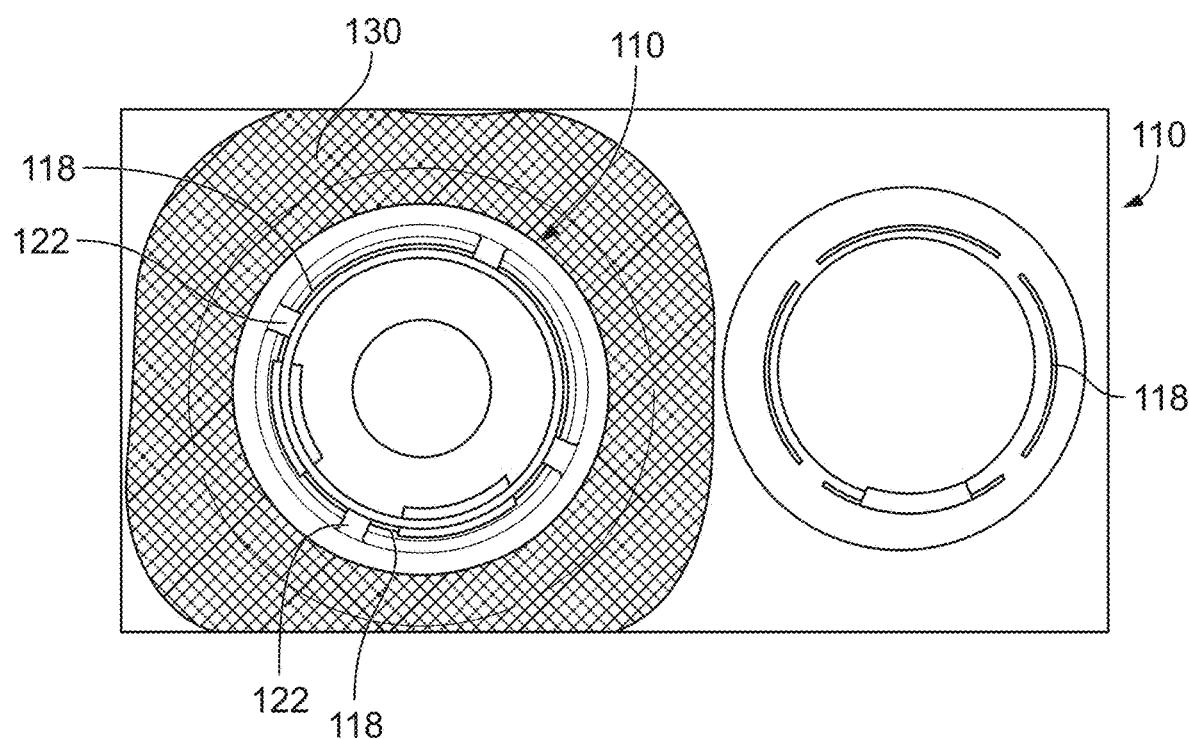
FIG. 6 is a body-side plan view of a ring member secured to an ostomy skin barrier (right) alongside a body-side view of a ring member (left) according to embodiments presented herein.

FIGS. 5 and 5A illustrate a further embodiment presented herein. As shown schematically in FIGS. 5 and 5A, a ring member 110 is provided having characteristics similar to that of ring member illustrated in FIGS. 1-2, except that said ring member 110 can comprise slotted windows 118 around the engagement portion 116. An insertable component 120 such as an insertable rib member can be insertable into slotted window(s) 118 and slidably adjusted to an area along engagement portion 116 requiring additional localize support for an adjacent portion of a peristomal area. As shown schematically in FIG. 5A, insertable component 120 can extend over an interior surface 134 of the ring member 110. FIG. 6 illustrates an additional plan view illustrating the ring members 110 of FIGS. 5 and 5A affixed to a barrier shield 130. As will be understood by persons of ordinary skill in the art, ring member 110 of FIGS. 5, 5A and 6 can have a plurality of slotted windows within the engagement portion 116 which are separated by one another by breaks 122 at opposing ends. The slotted windows can completely encircle the engagement portion 116 to enable variable placement of insertable component(s) 120 at multiple different locations around ring member 110. As shown schematically in FIG. 6, insertable components 120 can be slidably received within the slotted windows 118.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. An ostomy appliance comprising:
   a ring member having an interior surface and an engagement portion encircling a centrally-located input opening, the engagement portion comprising a plurality of spaced-apart flexible tabs extending radially inward into the input opening, the flexible tabs having opposing side edges and opposing interior and exterior surfaces with an opening extending therebetween, the opening being centrally located between the opposing side edges, a plurality of spaced-apart teeth extending radially inward from the inside surface of the ring member into the input opening, the teeth being in alignment in a first direction with spaces between the plurality of flexible tabs and having an inside surface facing the interior surface of the plurality of flexible tabs; and
   a rib member having a curved body portion with opposing inside and outside surfaces joined together by opposing top and bottom edges and opposing side edges, the rib member having a dowel, pins and a notched section in the body portion, the dowel extending radially inward from the inside surface of the body portion, the pins extending axially away from the top edge of the body portion, the notched section forming a recess along the inside surface and bottom edge of the body portion,
   wherein the rib member is removably securable to the ring member whereby the pins of the rib member are insertable into openings of adjacent flexible tabs of the plurality of flexible tabs and a first tooth of the plurality of spaced-apart teeth in alignment in the first direction with a space between the adjacent flexible tabs and is received within the notched section of the rib member, the notched section being seated on the inside surface of the tooth.

2. The ostomy appliance of claim 1 wherein the ring member further comprises an outer flange and a middle portion, the middle portion being between the outer flange and the engagement portion and being curved to elevate the engagement portion from the outer flange in the first direction.

3. The ostomy appliance of claim 1 wherein the plurality of spaced apart flexible tabs encircle the entirety of the engagement portion and the input opening, each of the plurality of spaced-apart tabs being substantially equivalent in size and being spaced a same distance apart from adjacent ones of the plurality of flexible tabs.

4. The ostomy appliance of claim 1 wherein a first distance separates the openings of the adjacent flexible tabs, the pins of the rib member being reciprocally spaced apart from one another by said first distance.

5. The ostomy appliance of claim 4 wherein the first tooth is spaced halfway between the openings of the adjacent flexible tabs in a second direction perpendicular to the first direction.

6. The ostomy appliance of claim 1 wherein the ring member is provided as an insert between layers of an ostomy barrier.

7. The ostomy appliance of claim 1 wherein the ring member is removably securable to an ostomy barrier securable to a user.

8. The ostomy appliance of claim 1 wherein the plurality of spaced-apart flexible tabs are curved.

9. The ostomy appliance of claim 1 wherein upon being applied to a user, the inside surface of the plurality of flexible tabs are configured to engage an adjacent parastomal region of the user and pull the adjacent parastomal region towards a pouch-side of the ring member.

10. The ostomy appliance of claim 1 wherein, upon the rib member being secured to the ring member, the adjacent flexible tabs have reduced flexibility.

11. The ostomy appliance of claim 1 further comprising a plurality of rib members substantially identical to the rib member, each of the plurality of rib members being removably securable and repositionable between adjacent tabs of the plurality of flexible tabs and a tooth of the plurality of spaced apart teeth positioned between the adjacent tabs.

12. A convex support for an ostomy appliance comprising:
an annular ring member having an interior surface and an engagement portion encircling a centrally-located input opening, the engagement portion comprising a plurality of spaced-apart flexible tabs extending radially inward into the input opening, the flexible tabs having opposing side edges and opposing interior and exterior surfaces with an opening extending therebetween, the opening being centrally located between the opposing side edges, a plurality of spaced-apart teeth extending radially inward from the inside surface of the ring member into the input opening, the teeth being in alignment in a first direction with spaces between the plurality of flexible tabs and having an inside surface facing the interior surface of the plurality of flexible tabs; and
a rib member having a curved body portion with opposing inside and outside surfaces joined together by opposing top and bottom edges and opposing side edges, the rib member having a dowel, pins and a notched section in the body portion, the dowel extending radially inward from the inside surface of the body portion, the pins extending axially away from the top edge of the body portion, the notched section forming a recess along the inside surface and bottom edge of the body portion,
wherein the rib member is removably securable to the ring member whereby the pins of the rib member are insertable into openings of adjacent flexible tabs of the plurality of flexible tabs and a first tooth of the plurality of spaced-apart teeth in alignment in the first direction with a space between the adjacent flexible tabs and is received within the notched section of the rib member, the notched section being seated on the inside surface of the tooth.

13. The convex support of claim 12 wherein the plurality of flexible tabs comprises sixteen tabs that encircle the entirety of the engagement portion and the input opening, each of the sixteen tabs being substantially equivalent in size and being spaced a same distance apart from one another.

14. The convex support of claim 1 wherein the plurality of spaced-apart teeth comprises sixteen teeth equivalently spaced apart from one another around the interior side of the ring member.

15. The convex support of claim 14 further comprising a plurality of rib members substantially identical to the rib member, the plurality of rib members being of a quantity between two and eight.

16. The convex support of claim 12 wherein the plurality of spaced-apart teeth comprise a distal end having an elevated barbed section to retain the rib member thereon.

17. The convex support of claim 12 wherein the plurality of spaced-apart teeth comprises the first tooth, a second tooth and a third tooth located in sequence along a portion of the ring member and the plurality of spaced apart flexible tabs comprises a first and second tab, wherein the first tab is aligned in the first direction between the first tooth and the second tooth and the second tab is aligned in the first direction between the second tooth and the third tooth.

18. The convex support of claim 17 wherein upon the rib member being secured to the ring member, a first portion of the bottom edge of the body portion is between the first tooth and the second tooth and a second potion of the bottom edge of the body portion is between the second tooth and the third tooth.

19. The convex support of claim 18 wherein the rib member comprises a first rib member and the convex support further comprises a second rib member substantially identical to the first rib member, wherein the first and second rib members are securable to the ring member in adjacent positions alongside one another and upon being secured in the adjacent positions, the first tooth is between one of the opposing side edges of the first rib member and one of an opposing side edge of the second rib member.

20. The convex support of claim 12 wherein the rib member is securable to the ring member by being snap fit thereon whereby the outside surface of the rib member snaps into place against the interior surface of the ring member.

\* \* \* \* \*

UNITED STATES PATENT AND TRADEMARK OFFICE
CERTIFICATE OF CORRECTION

| | |
|---|---|
| PATENT NO. | : 11,918,508 B1 |
| APPLICATION NO. | : 18/263616 |
| DATED | : March 5, 2024 |
| INVENTOR(S) | : James P. Wines |

It is certified that error appears in the above-identified patent and that said Letters Patent is hereby corrected as shown below:

On the Title Page

On Page 2, in Item (56), under "OTHER PUBLICATIONS", in Column 2, Line 1, delete "ssued" and insert -- issued --, therefor.

In the Specification

In Column 3, Line 57, delete "potion" and insert -- portion --, therefor.

In Column 4, Line 39, delete "described" and insert -- described as --, therefor.

In Column 5, Line 23, delete "potion" and insert -- portion --, therefor.

In Column 5, Line 46, delete "illustrates" and insert -- illustrate --, therefor.

In Column 5, Line 47, delete "and." and insert -- and --, therefor.

In Column 5, Line 50, delete "member" and insert -- member 10. --, therefor.

In Column 5, Line 61, delete "FIG. 1-2," and insert -- FIGS. 1-2, --, therefor.

In Column 5, Line 61, delete "member" and insert -- member 10 --, therefor.

In Column 6, Line 8, delete "member." and insert -- member 10. --, therefor.

In Column 6, Line 13, delete "dowel" and insert -- dowel 50 --, therefor.

In Column 6, Line 18, delete "both of" and insert -- both --, therefor.

In Column 6, Lines 38-39, delete "half way" and insert -- halfway --, therefor.

Signed and Sealed this
Fourth Day of June, 2024

Katherine Kelly Vidal
*Director of the United States Patent and Trademark Office*

In Column 6, Line 49, delete "member" and insert -- member 40 --, therefor.

In Column 6, Line 52, delete "member" and insert -- member 40 --, therefor.

In Column 7, Line 4, delete "member is" and insert -- member 40 is --, therefor.

In the Claims

In Column 10, Line 26, in Claim 14, delete "claim 1" and insert -- claim 12 --, therefor.

In Column 10, Line 48, in Claim 18, delete "potion" and insert -- portion --, therefor.